US012612346B2

(12) United States Patent
Wiederhold et al.

(10) Patent No.: US 12,612,346 B2
(45) Date of Patent: Apr. 28, 2026

(54) METHOD FOR THE PREPARATION OF 1,2-PROPANEDIOL

(71) Applicant: Evonik Operations GmbH, Essen (DE)

(72) Inventors: Holger Wiederhold, Darmstadt (DE); David Bolz, Frankfurt (DE); Georg Friedrich Thiele, Friedberg (DE); Bernd Jaeger, Bickenbach (DE); Hans-Jürgen Köhle, Mainhausen (DE); Sebastian Imm, Bad Vilbel (DE); Marina Lazar, Hasselroth (DE)

(73) Assignee: Evonik Operations GmbH, Essen (DE)

( * ) Notice: Subject to any disclaimer, the term of this patent is extended or adjusted under 35 U.S.C. 154(b) by 534 days.

(21) Appl. No.: 18/249,908

(22) PCT Filed: Oct. 7, 2021

(86) PCT No.: PCT/EP2021/077710
§ 371 (c)(1),
(2) Date: Apr. 20, 2023

(87) PCT Pub. No.: WO2022/084055
PCT Pub. Date: Apr. 28, 2022

(65) Prior Publication Data
US 2023/0382829 A1 Nov. 30, 2023

(30) Foreign Application Priority Data
Oct. 21, 2020 (EP) ..................................... 20202956

(51) Int. Cl.
*C07C 29/04* (2006.01)
*B01D 3/14* (2006.01)
*B01D 61/02* (2006.01)
*B01J 31/02* (2006.01)
*C07C 29/86* (2006.01)

(52) U.S. Cl.
CPC .............. *C07C 29/04* (2013.01); *B01D 3/143* (2013.01); *B01D 61/027* (2013.01); *B01J 31/0239* (2013.01); *C07C 29/86* (2013.01)

(58) Field of Classification Search
CPC .............................. C07C 29/48; C07C 31/205
USPC ......................................................... 568/360
See application file for complete search history.

(56) References Cited

U.S. PATENT DOCUMENTS

| | | |
|---|---|---|
| 4,308,409 A | 12/1981 | Wu et al. |
| 10,214,471 B2 | 2/2019 | Wiederhold et al. |
| 2007/0007195 A1 | 1/2007 | Ebert et al. |
| 2012/0296102 A1 | 11/2012 | Kawabata et al. |
| 2018/0057473 A1 | 3/2018 | Stock et al. |
| 2018/0354878 A1 | 12/2018 | Wiederhold et al. |

FOREIGN PATENT DOCUMENTS

| | | |
|---|---|---|
| CN | 102725276 A | 10/2012 |
| EP | 1741481 | 1/2007 |
| TW | 201702237 A | 1/2017 |
| WO | 2017/089075 | 6/2017 |

OTHER PUBLICATIONS

International Search Report dated Dec. 23, 2021, in PCT/EP2021/077710, 5 pages.
Written Opinion dated Dec. 23, 2021, in PCT/EP2021/077710, 7 pages.
U.S. Appl. No. 18/249,984, Apr. 21, 2023, Wiederhold et al.
U.S. Appl. No. 18/249,724, Apr. 19, 2023, Wiederhold et al.
U.S. Appl. No. 18/249,980, Apr. 21, 2023, Wiederhold et al.
U.S. Appl. No. 18/249,584, Apr. 19, 2023, Wiederhold et al.
U.S. Appl. No. 18/249,695, Apr. 19, 2023, Wiederhold et al.
U.S. Appl. No. 18/249,729, Apr. 19, 2023, Bolz et al.
U.S. Appl. No. 18/249,982, Apr. 21, 2023, Wiederhold et al.
U.S. Appl. No. 18/249,660, Apr. 19, 2023, Wiederhold et al.
U.S. Appl. No. 18/249,906, Apr. 20, 2023, Wiederhold et al.
U.S. Appl. No. 18/249,825, Apr. 20, 2023, Wiederhold et al.
Office action received for Taiwanese Patent Application No. 110138536, mailed on Mar. 6, 2025, 5 pages.

*Primary Examiner* — Ana Z Muresan
(74) *Attorney, Agent, or Firm* — Grüneberg Global IP, PLLC

(57) ABSTRACT

A method for preparing 1,2-propanediol involves reacting propene with hydrogen peroxide, in the presence of a phase transfer catalyst and a heteropolytungstate, in a liquid reaction mixture containing an aqueous phase with a maximum apparent pH of 6 and an organic phase containing a solvent having a solubility in water at 20° C. of less than 500 mg/kg. The method then involves separating the liquid reaction mixture into an aqueous phase containing 1,2-propanediol and an organic phase; recycling at least a part of the separated organic phase to the reaction; and extracting the separated aqueous phase with an extractant solution containing the same phase transfer catalyst and solvent as used in the reaction to provide an extracted aqueous phase and an extract phase. The method further involves recycling at least a part of the extract phase to the reaction and recovering 1,2-propanediol from the extracted aqueous phase.

14 Claims, 1 Drawing Sheet

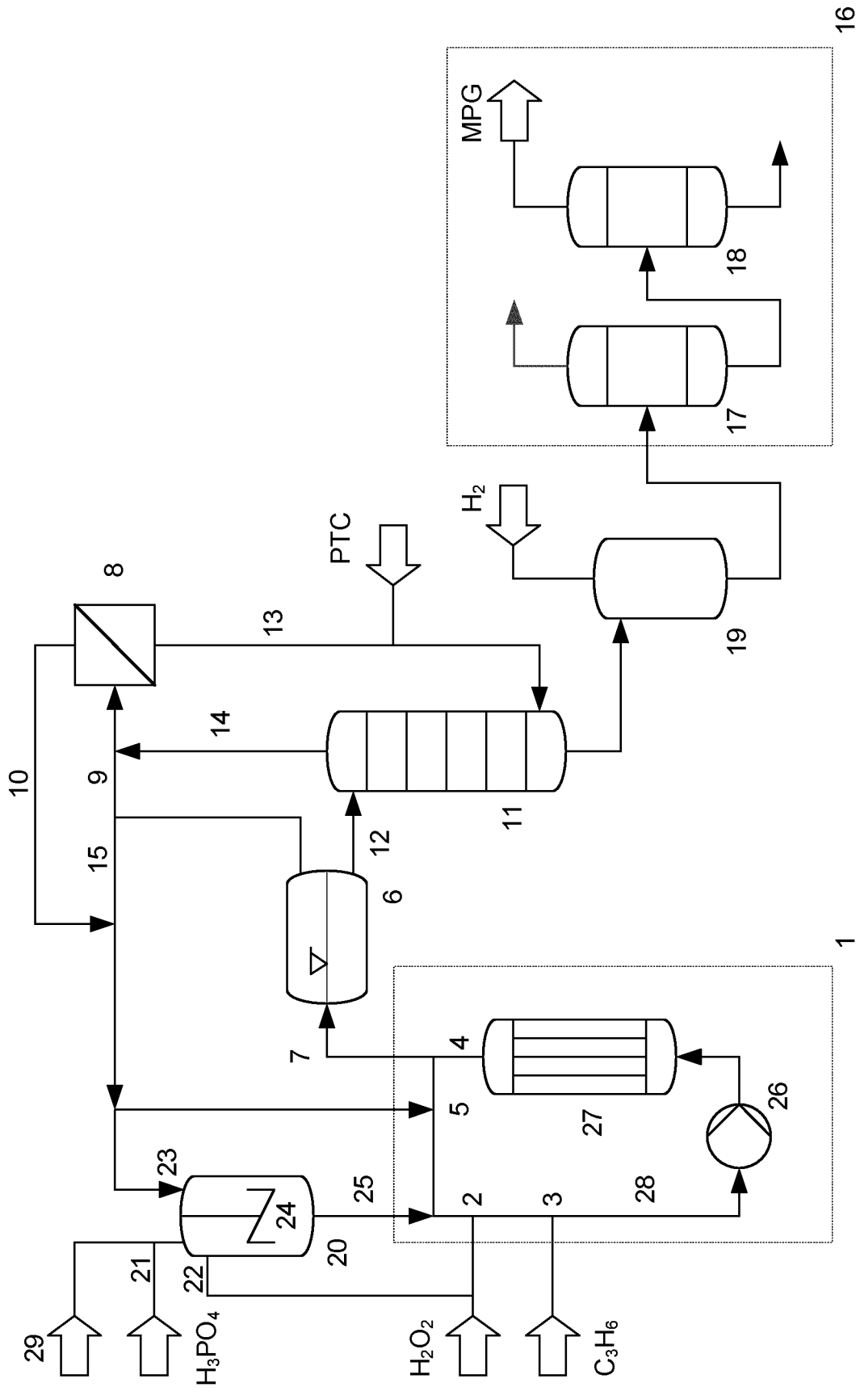

METHOD FOR THE PREPARATION OF 1,2-PROPANEDIOL

CROSS-REFERENCE TO RELATED APPLICATIONS

This application the National Stage entry under § 371 of International Application No. PCT/EP2021/077710, filed on Oct. 7, 2021, and which claims the benefit of priority to European Application No. 20202956.7, filed on Oct. 21, 2020. The content of each of these applications is hereby incorporated by reference in its entirety.

BACKGROUND OF THE INVENTION

Field of the invention

The present invention relates to a method for the preparation of 1,2-propanediol by reacting propene with hydrogen peroxide.

DESCRIPTION OF RELATED ART

In a well-established process used in the industry, 1,2-propanediol is prepared by reacting propene oxide with water. Propene oxide can be made on an industrial basis using the HPPO process comprising the reaction of propene with hydrogen peroxide in the presence of a titanium zeolite catalyst and an organic solvent. Propene oxide is then isolated and purified prior to the step of reacting it with water to make 1,2-propanediol.

WO 2017/089075 discloses a method for producing 1,2-propanediol from propene and hydrogen peroxide comprising: a) reacting propene with hydrogen peroxide in the presence of a catalyst mixture comprising a phase transfer catalyst and a heteropolytungstate, wherein the reaction is carried out in a liquid mixture comprising an aqueous phase with a maximum pH of 6 and an organic phase, b) dividing the two-phase mixture from step a) into an aqueous phase and an organic phase containing propylene oxide, c) returning the propylene oxide contained in the separated organic phase into the reaction from step a) and d) separating 1,2-propanediol from the aqueous phase separated in step b).

In the process of WO 2017/089075, the tungstates contained in the aqueous phase of the reaction mixture will end up in the residual bottoms product obtained in the distillative recovery of 1,2-propanediol from the aqueous phase and will either be lost with this bottoms product or have to be recovered from this bottoms product.

SUMMARY OF THE INVENTION

The inventors of the present invention have now found that extracting the aqueous phase resulting from the propene oxidation reaction with an extractant solution comprising the phase transfer catalyst and the solvent used in the oxidation reaction and recycling all or a part of the extract phase to the oxidation reaction can considerably reduce losses of tungstate with the aqueous phase of the propene oxidation reaction mixture without any need for recovering tungstate from bottoms products of a distillation used for recovery of 1,2-propanediol.

Subject of the invention is therefore a method for the preparation of 1,2-propanediol comprising:

a) reacting propene with hydrogen peroxide in the presence of a catalyst mixture comprising a phase transfer catalyst and a heteropolytungstate in a liquid reaction mixture comprising an aqueous phase with a maximum apparent pH of 6 and an organic phase comprising a solvent (S) having a solubility in water at 20° C. of less than 500 mg/kg;

b) separating the liquid reaction mixture of step a) into an aqueous phase ($P_a$) comprising 1,2-propanediol and an organic phase ($P_o$);

c) recycling at least a part of the separated organic phase ($P_o$) to the reaction step a); d) extracting the separated aqueous phase ($P_a$) with an extractant solution comprising the same phase transfer catalyst and the same solvent (S) as used in step a) to provide an extracted aqueous phase ($P_{ae}$) and an extract phase ($P_e$) comprising a salt of the phase transfer catalyst and a heteropolytungstate or tungstate;

e) recycling at least a part of the extract phase ($P_e$) to step a); and f) recovering 1,2-propanediol from the extracted aqueous phase ($P_{ae}$).

A further subject of the invention is a facility for preparing 1,2-propanediol, comprising:

a) a cooled loop reactor comprising an inlet for hydrogen peroxide, an inlet for propene, an outlet for reaction mixture, and at least one recycle stream inlet;

b) a phase separator comprising an inlet, a first outlet for separated aqueous phase and a second outlet for separated organic phase, the inlet being connected by a conduit to the outlet of the loop reactor for receiving reaction mixture;

c) a membrane nanofiltration unit having an inlet, a first outlet for retentate and a second outlet for permeate, the inlet being connected by a conduit to the second outlet of the phase separator for receiving all or a part of the separated organic phase and the first outlet being connected by a conduit to a recycle stream inlet of the loop reactor;

d) an extraction unit, having a feed inlet connected by a conduit to the first outlet of the phase separator for receiving the separated aqueous phase, an extractant inlet connected by a conduit to the second outlet of the membrane nanofiltration unit for receiving the permeate, an extract outlet and a raffinate outlet;

e) a first recycle conduit connecting the extract outlet of the extraction unit with the inlet of the membrane nanofiltration unit and/or a recycle stream inlet of the loop reactor;

f) optionally a second recycle conduit connecting the second outlet of the phase separator to an inlet of the loop reactor for receiving the fraction of the separated organic phase which is not passed to the membrane nanofiltration unit as a recycle stream; and g) a separation unit, having an inlet connected to the raffinate outlet of the extraction unit, an outlet for separated water, an outlet for separated 1,2-propanediol and an outlet for by-products.

BRIEF DESCRIPTION OF DRAWINGS

The FIGURE shows an embodiment of a facility of the invention with a counter current extraction column in the extraction unit, a hydrogenation unit and two distillation columns in the separation unit, and an additional catalyst reactivation unit.

DETAILED DESCRIPTION OF THE INVENTION

In the method of the present invention, propene is reacted in a step a) with hydrogen peroxide in the presence of a catalyst mixture comprising a phase transfer catalyst and a heteropolytungstate. This reaction is carried out in a liquid reaction mixture which comprises an aqueous phase with a maximum apparent pH of 6 and an organic phase which comprises a solvent (S) having a solubility in water at 20° C. of less than 500 mg/kg.

Propene can be used in pure form or in a mixture with propane, wherein the proportion of propane may be up to 20 mol-%. The proportion of propane in the propene used is preferably less than 5 mol-%. Propene is preferably employed in a molar excess to hydrogen peroxide, preferably in a molar ratio of propene to hydrogen peroxide of from 1.1:1 to 10:1.

Hydrogen peroxide is preferably used in the form of an aqueous solution, preferably with a hydrogen peroxide content of 10 to 80% by weight, particularly preferably 30 to 70% by weight. Any commercially available grade of aqueous hydrogen peroxide solutions can be used. A crude hydrogen peroxide product obtained in the extraction stage of the anthraquinone process for producing hydrogen peroxide may also be used.

The catalyst mixture used in step a) comprises a heteropolytungstate. The heteroatom is preferably phosphorus or arsenic and is particularly preferably phosphorus, i.e. the heteropolytungstate is particularly preferably a polytungstophosphate. Heteropolytungstates are well known to a person skilled in the art. Preferred polytungstophosphates have a molar ratio of phosphorus to tungsten in the range of from 1:2 to 1:12. The polytungstophosphate is preferably generated in situ by combining phosphoric acid and sodium tungstate, which can be carried out in the liquid reaction mixture itself or prior to adding the polytungstophosphate to the liquid reaction mixture. Phosphoric acid and sodium tungstate are preferably employed at a molar ratio of phosphorus to tungsten in the range of from 1:2 to 10:1, preferably from 4:1 to 8:1. The heteropolytungstate reacts with hydrogen peroxide in the liquid reaction mixture to form peroxotungstates and peroxotungstophosphates, for example $PO_4[WO(O_2)_2]_4^{3-}$ and $HPO_4[WO(O_2)_2]_2^{2-}$ as well as partially protonated forms thereof, which are presumably the catalytically active species for oxidizing propene.

The catalyst mixture used in step a) also comprises a phase transfer catalyst. The phase transfer catalyst comprises a cation or a compound which forms a cation in the aqueous phase, whereby the cation can form a salt with a peroxotungstate or heteropolyperoxotungstate, which salt is soluble in the organic phase of the liquid reaction mixture. The phase transfer catalyst preferably comprises a singly-charged cation or a compound which forms a singly-charged cation in the aqueous phase. Suitable as phase transfer catalyst are tertiary amines, tertiary and quaternary ammonium salts, and quaternary phosphonium salts. Suitable counterions for tertiary and quaternary ammonium salts are the anions chloride, bromide, nitrate, sulphate, hydrogen phosphate, dihydrogen phosphate, methyl sulfonate, methyl sulphate and ethyl sulphate. The phase transfer catalyst is preferably used in an amount which results in a molar ratio in the liquid mixture of phase transfer catalyst to tungsten in the range of from 0.2:1 to 3:1 and particularly preferably of from 0.4:1 to 1:1, where the molar ratio refers to the cations or compounds forming cations in the employed phase transfer catalyst and to the employed amount of tungsten.

In a preferred embodiment, the phase transfer catalyst is a tertiary amine or a tertiary or a quaternary ammonium salt which comprises in total at least 12 carbon atoms, preferably from 12 to 60 carbon atoms. Preferred are tetraalkylammonium salts. Suitable tertiary amines are for example dodecyldimethylamine, hexadecyldimethylamine, octadecyldimethylamine, tributylamine and trioctylamine. Suitable tertiary ammonium salts are the protonation products of these tertiary amines. Suitable quaternary ammonium salts are for example dodecyltrimethylammonium salts, hexadecyltrimethylammonium salts, octadecyltrimethylammonium salts, methyltributylammonium salts and methyltrioctylammonium salts. More preferably, the phase transfer catalyst comprises a tertiary or quaternary ammonium ion having the structure $R^1R^2R^3NR^{4+}$, wherein $R^1$, $R^2$ and $R^3$ are the same or different and are each selected from alkyl groups having from 8 to 10 carbon atoms and $R^4$ is hydrogen or methyl. Most preferably, the phase transfer catalyst comprises methyltri(octyl/decyl)ammonium methylsulfate (CAS No. 2387913-24-6).

In another preferred embodiment, the phase transfer catalyst comprises at least one salt having a tertiary or quaternary ammonium ion of the structure $R^1R^2R^3R^4N^+$, where $R^1$ is a $Y—O(C═O)R^5$ group with Y being $CH_2CH_2$, $CH(CH_3)CH_2$ or $CH_2CH(CH_3)$ and $R^5$ being an alkyl group or alkenyl group having 11 to 21 carbon atoms, $R^2$ is hydrogen or an alkyl group having 1 to 4 carbon atoms, and $R^3$ and $R^4$ are each independently $R^1$, an alkyl group having 1 to 4 carbon atoms or $Y—OH$.

Preferred are quaternary ammonium salts with methylsulphate as the counterion, where $R^2$ is a methyl group and $R^5$ is a linear alkyl group or alkenyl group. Particularly preferred are the salts $(CH_3)_3N^+CH_2CH_2O(C═O)R^5$ $CH_3OSO_3^-$, $(CH_3)_2N+(CH_2CH_2OH)(CH_2CH_2O(C═O)R^5)$ $CH_3OSO_3^-$, $(CH_3)_2N^+(CH_2CH_2O(C═O)R^5)_2$ $CH_3OSO_3^-$, $CH_3N^+(CH_2CH_2OH)_2(CH_2CH_2O(C═O)R^5)$ $CH_3OSO_3^-$, $CH_3N^+(CH_2CH_2OH)(CH_2CH_2O(C═O)R^5)_2$ $CH_3OSO_3^-$, $CH_3N^+(CH_2CH_2O(C═O)R^5)_3$ $CH_3OSO_3^-$, $(CH_3)_3N^+$ $CH_2CH(CH_3)O(C═O)R^5$ $CH_3OSO_3^-$, $(CH_3)_2N^+(CH_2CH(CH_3)OH)(CH_2CH(CH_3)O(C═O)R^5)$ $CH_3OSO_3^-$ and $(CH_3)_2N^+(CH_2CH(CH_3)O(C═O)R^5)_2$ $CH_3OSO_3^-$, in which $R^5$ is in each case a linear alkyl group or alkenyl group having 11 to 21 carbon atoms. Most preferred is the salt $(CH_3)_2N^+(CH_2CH(CH_3)O(C═O)R^5)_2$ $CH_3OSO_3^-$ in which $R^5$ is an alkyl group or alkenyl group having 11 to 17 carbon atoms. The phase transfer catalysts of this embodiment may be prepared by esterifying ethanolamine, isopropanolamine, diethanolamine, diisopropanolamine, triethanolamine or triisopropanolamine with a fatty acid and subsequent quaternization with dimethyl sulphate. These phase transfer catalysts have the advantage that they are readily biodegradable, unlike tetraalkylammonium salts, and can be introduced into a biological treatment plant without further pretreatment. The salts with methylsulphate as anion are also less corrosive than tetraalkylammonium halides.

The reaction of step a) is carried out in a liquid reaction mixture which comprises two liquid phases, an aqueous phase with a maximum apparent pH of 6 and an organic phase which comprises a solvent (S) having a solubility in water at 20° C. of less than 500 mg/kg. The term "apparent pH" here refers to a value determined by measurement with a glass electrode employing a commercial pH meter calibrated with aqueous buffer solutions of known pH for measuring dilute aqueous solutions. This apparent pH differs from the notional pH, i.e. the negative logarithm of the hydrogen ion activity, by a constant value because the normal potential of the glass electrode in the aqueous phase of the reaction mixture, which comprises hydrogen peroxide and glycols, is different than the normal potential in pure water. The apparent pH of the aqueous phase is preferably maintained in the range from 1.0 to 3.5, particularly preferably in the range from 2.0 to 3.0. The apparent pH can be maintained in this range by addition of acid, preferably sulphuric acid or phosphoric acid, or by addition of base, preferably aqueous sodium hydroxide solution. Adjusting the apparent pH in the preferred range provides high selectivity for 1,2-propanediol and prevents enriching propene oxide in the aqueous phase, which simplifies the subsequent separation of propylene glycols from the aqueous phase.

In the reaction step a) the weight ratio of hydrogen peroxide to water fed to step a) is preferably adjusted while maintaining a molar excess of propene to hydrogen peroxide fed to step a). The weight ratio of hydrogen peroxide to water is preferably varied within the range of from 0.05 to 1.5, more preferably from 0.10 to 0.7 and most preferably from 0.15 to 0.45. The molar ratio of propene to hydrogen peroxide fed to step a) is preferably from 1.1:1 to 10:1, more preferably from 1.2:1 to 4:1.

The reaction is preferably conducted at a temperature in the range of from 50 to 110° C., more preferably 60 to 100° C. and particularly preferably 70 to 90° C. The reaction pressure is preferably higher than the vapor pressure of propene at the reaction temperature to ensure that most of the propene is present in the liquid organic phase of the liquid mixture.

The reaction of step a) is carried out in a liquid reaction mixture with an organic phase comprising a solvent (S) which has a solubility in water of less than 500 mg/kg at 20° C., preferably less than 250 mg/kg at 20° C. The solvent preferably has a boiling point of more than 100° C., preferably more than 120° C. Suitable as solvents are alcohols having one or more hydroxyl groups, ethers, esters, ketones and alkylated aromatic hydrocarbons. The solvent improves extraction of a salt formed of the heteropolytungstate and the phase transfer catalyst into the organic phase present in step a). Preferably the amount of solvent (S) is selected to provide a proportion of solvent (S) in the organic phase during the reaction in the range of from 10 to 90% by weight.

The solvent preferably comprises at least one alkylated aromatic hydrocarbon having 7 to 12 carbon atoms. Suitable alkylated aromatic hydrocarbons are, for example, toluene, 1,2-dimethylbenzene (o-xylene), 1,3-dimethylbenzene (m-xylene), 1,4-dimethylbenzene (p-xylene), ethylbenzene, 1,2,3-trimethylbenzene, 1,2,4-trimethylbenzene, 1,3,5-trimethylbenzene (mesitylene), 1-ethyl-2-methylbenzene, 1-ethyl-3-methylbenzene and 1-ethyl-4-methylbenzene and n-propylbenzene. Preferably, hydrocarbon mixtures comprising more than 50% by weight, particularly preferably more than 80% by weight, of alkylated aromatic hydrocarbons having 7 to 12 carbon atoms are used as solvent. The use of these solvents enables extracting most of the peroxotungstates into the organic phase of the reaction mixture and recycling them to step a) with the organic phase of the reaction mixture. The phase transfer catalyst, the molar ratio of phase transfer catalyst to heteropolytungstate, the molar ratio of heteroatom of the heteropolytungstate to tungsten, the molar ratio of propene to hydrogen peroxide and the amount of solvent are then preferably selected to transfer as much as possible of the tungsten present in the liquid reaction mixture into the organic phase.

The phase transfer catalyst, the heteropolytungstate and the solvent (S) can be added in step a) of the method of the present invention separately or in the form of mixtures containing two or all three of these components. Preferably, the phase transfer catalyst and the heteropolytungstate are added dissolved in an organic phase comprising the solvent (S).

The reaction of step a) may be carried out in batch or continuously, with a continuous reaction being preferred. The concentration of hydrogen peroxide in the aqueous phase is preferably maintained in the range of 0.1 to 5% by weight, particularly preferably 0.5 to 3% by weight. The concentration of hydrogen peroxide can be adjusted in this range by appropriate selection of the reaction temperature, the molar ratio of propene to hydrogen peroxide and the residence time of the liquid mixture in the reactor in which the reaction takes place. The residence time of the reaction mixture is preferably adjusted to maintain a hydrogen peroxide conversion in the range of from 80 to 99%.

During the reaction, the liquid mixture is preferably mixed in order to generate a large phase interface between the aqueous phase and the organic phase. For this purpose, the reaction is preferably carried out continuously in a loop reactor which has fixed internals in a tubular section and the liquid mixture is passed through the loop reactor at a flow rate which generates a turbulent flow at the internals. Baffles, static mixing elements, structured packings or random packings can be used as internals for this purpose. In combination to these internals or as an alternative, heat exchangers, such as plate heat exchangers or tube bundle heat exchangers, may be used, in which turbulent flow is generated, for example between the plates of a plate heat exchanger or in the tubes of a tube bundle heat exchanger.

Preferably, all or a part of the reaction heat generated in step a) is removed while the reaction proceeds, preferably by cooling the reaction mixture in a heat exchanger. More preferably, the reaction is carried out continuously in a loop reactor which comprises a heat exchanger within the reactor loop for cooling the reaction mixture.

In step b) of the method of the present invention, the liquid reaction mixture provided by step a) is separated into an aqueous phase ($P_a$) comprising 1,2-propanediol and an organic phase ($P_o$). The separation of the two-phase reaction mixture provided by step a) is preferably carried out in a settler vessel. The two-phase reaction mixture is preferably passed through a coalescer element comprising a structured packing or a random packing with a surface wetted by the dispersed phase of the two-phase mixture in order to achieve a more complete separation.

The aqueous phase ($P_a$) typically comprises water, unreacted hydrogen peroxide and the reaction product 1,2-propanediol. The aqueous phase typically also contains dipropylene glycol and tripropylene glycol as well as reaction byproducts, such as 1-hydroperoxy-2-propanol and 2-hydroperoxy-1-propanol formed by reaction of propene oxide with hydrogen peroxide, and formic acid, acetic acid and hydroxyacetone formed by further oxidation of 1,2-propanediol. The aqueous phase typically may also comprise phosphoric acid and sodium salts of phosphoric acid if a polytungstophosphate generated in situ by combining phosphoric acid and sodium tungstate is used in step a). The organic phase ($P_o$) comprises the solvent (S) as well as unreacted propene and propene oxide that is formed as intermediate when propene is reacted with hydrogen peroxide and has not been hydrolyzed to 1,2-propanediol. The organic phase ($P_o$) typically also comprises one or more salts formed of the heteropolytungstate and the cation of the phase transfer catalyst. The organic phase $P_o$ will also comprise propane, if the propene starting material contains propane.

In step c) of the method of the present invention, at least a part of the separated organic phase ($P_o$) is recycled to the reaction step a). Thereby, propene oxide present in the organic phase ($P_o$) is recycled to step a) in order to achieve a complete conversion of propene to 1,2-propanediol, dipropylene glycol and tripropylene glycol. Preferably, the heteropolytungstate present in the organic phase ($P_o$) is recycled into step a), and it is particularly preferred to recycle substantially all of the catalyst mixture that is present in the organic phase into step a).

In a preferred embodiment, step c) comprises a step of contacting a part or all of the separated organic phase ($P_o$) with an aqueous reactivating solution comprising hydrogen peroxide and phosphoric acid at a temperature of from 5 to 40° C. In this catalyst reactivating step, phosphoric acid is preferably employed at a molar ratio of phosphorus to tungsten contained in the organic phase ($P_o$) in the range of from 1:2 to 10:1, preferably from 4:1 to 8:1. The aqueous phase of the liquid mixture formed in the catalyst reactivating step preferably comprise from 10 to 40% by weight, more preferably 15 to 38% by weight and most preferred 18 to 35% by weight of phosphoric acid. Hydrogen peroxide is preferably used in an amount providing at least 2 mol hydrogen peroxide per mol tungsten, preferably from 2 to 10 mol hydrogen peroxide per mol tungsten. It is believed that the preferred molar ratio of phosphorus to tungsten and hydrogen peroxide to tungsten and the preferred concentration of phosphoric acid in the aqueous phase convert most of the tungstate to peroxotungstophosphates of formula $PO_4[WO(O_2)_2]_4^{3-}$ and $HPO_4[WO(O_2)_2]_2^{2-}$ as well as partially protonated forms thereof, which are presumably the catalytically most active species for oxidizing propene. The temperature of from 5 to 40° C. used in the catalyst reactivating step prevents decomposition and formation of molecular oxygen from these species before they are passed to reaction step a). Preferably, the catalyst reactivating step is conducted at a temperature of from 10 to 35° C., more preferably 15 to 30° C. The reaction time in the catalyst reactivating step is typically from 1 to 200 min, preferably 1 to 20 min and more preferably 2 to 10 min, with reaction times of less than 20 min being preferred at the upper end of the temperature range of from 5 to 40° C. if the organic phase ($P_o$) comprises propene. Only a small part of propene present in the liquid mixture of the catalyst reactivating step will then be oxidized, the catalyst reactivating step can be carried out without cooling and essentially all of the peroxotungstophosphates generated in the catalyst reactivating step can be passed to step a). The organic phase resulting from the catalyst reactivating step is preferably passed to reaction step a) without any intervening steps.

The organic phase ($P_o$) separated from the liquid reaction mixture provided by step a) may be recycled to step a) without further treatment. If the propene fed to step a) contains propane, it is preferred to separate a stream of unreacted propene from the organic phase in step c) before the organic phase is recycled to step a), with the separated stream of unreacted propene containing as much propane as the impure propene fed to step a). This way, an accumulation of propane in the organic phase of the reaction mixture of step a) can be avoided for a continuous reaction. The separated stream of unreacted propene may be passed to a C3 splitter for separating propene and propane and the recovered propene may be recycled to step a).

In step d) of the method of the present invention, the separated aqueous phase ($P_a$) is extracted with an extractant solution which comprises the same phase transfer catalyst and the same solvent (S) as used in step a). This extraction provides an extracted aqueous phase ($P_{ae}$) and an extract phase ($P_e$) which comprises a salt of the phase transfer catalyst and a heteropolytungstate or tungstate. The extraction may be carried out in an extraction unit comprising a mixer and a settler in series or in a series of from 2 to 5 consecutive extraction units each comprising a mixer and a settler in series. Alternatively, the extraction may be carried out in an extraction column. The extraction is preferably carried out with counter current flow of aqueous phase ($P_a$) and extractant solution, preferably in a counter current extraction column or in a series of extraction units each comprising a mixer and a settler with counter current flow along the series of extraction units. The extractant solution preferably comprises the phase transfer catalyst in an amount providing a molar ratio of phase transfer catalyst contained in the extractant solution to tungsten contained in the aqueous phase ($P_a$) in the range of from 1:1 to 100:1. The amount of extractant solution and phase transfer catalyst and, if a multistage extraction is used, the number of extraction stages or theoretical stages in an extraction column are selected to extract of from 25 to 90% of the tungsten contained in the aqueous phase ($P_a$) into the extract phase ($P_e$). The fraction of tungsten extracted into the extract phase ($P_e$) can be increased by increasing the volume ratio between extractant solution and aqueous phase ($P_a$), increasing the concentration of phase transfer catalyst in the extractant solution, increasing the number of extraction stages in a counter current extraction, or any combination thereof. The extracted aqueous phase ($P_{ae}$) may be passed through a coalescer for coalescing droplets of extractant solution dispersed in the extracted aqueous phase ($P_{ae}$). The organic phase formed by coalescing these droplets is preferably combined with the extract phase ($P_e$).

In step e) of the method of the present invention, at least a part of the extract phase ($P_e$) obtained in step d) is recycled to step a). Preferably, the extract phase ($P_e$) is combined with all or a part of the organic phase ($P_o$) separated in step b) prior to recycling it to step a). When the method of the invention comprises a catalyst reactivating step as described above, the extract phase ($P_e$) is preferably combined with the organic phase ($P_o$) prior to the catalyst reactivating step.

In step f) of the method of the present invention, 1,2-propanediol and dipropylene glycol are recovered from the extracted aqueous phase ($P_{ae}$) provided in step d). 1,2-Propanediol and dipropylene glycol are preferably recovered by a sequence of distillation steps. Preferably, a sequence of distillation steps as described in Ullmann's Encyclopedia of Industrial Chemistry, online edition, entry "Propanediols", page 4, DOI 10.1002/14356007.a22_163.pub2 is used where an overhead product comprising water is separated from a bottoms product comprising 1,2-propanediol and dipropylene glycol in a series two to four heat integrated distillation steps, followed by successive vacuum distillation steps which provide 1,2-propanediol and dipropylene glycol as overhead products and a bottoms product containing higher boiling organic compounds and salts. From this bottoms product, tripropylene glycol may be recovered as an overhead product in a further vacuum distillation step. The extraction step d) allows for reducing the content of tungsten in the extracted aqueous phase ($P_{ae}$) to a level where a recovery of tungsten in step f) or from a by-product stream of step f is no longer necessary for a resource efficient and economical operation of the process.

In a preferred embodiment, step f comprises an additional step of subjecting the extracted aqueous phase ($P_{ae}$) to a hydrogenation treatment before recovering 1,2-propanediol. The hydrogenation is preferably carried out using a supported hydrogenation catalyst comprising one or more metals from the group of Ru, Rh, Pd, Pt, Ag, Ir, Fe, Cu, Ni and Co on a support, wherein activated carbon, $SiO_2$, $TiO_2$, $ZrO_2$, $Al_2O_3$ and aluminium silicates are preferred as support materials. Preference is given to hydrogenation catalysts comprising ruthenium as active metal.

The catalytic hydrogenation is preferably carried out at a partial hydrogen pressure of 5 to 50 bar, preferably 5 to 35 bar, more preferred 7 to 30 bar, even more preferred 8 to 25 bar, and a temperature of 80° C. to 140° C., preferably 90° C. to 120° C. The hydrogenation catalyst may be used as a suspension or as a fixed bed, a trickle bed hydrogenation with a fixed bed catalyst being preferred. The hydrogenation can prevent problems caused by decomposition of hydrogen peroxide, which has not reacted in step a), in distillation steps for recovering 1,2-propanediol and dipropylene glycol. The hydrogenation also converts the by-products 1-hydroperoxy-2-propanol, 2-hydroperoxy-1-propanol and hydroxyacetone formed in step a) to 1,2-propanediol and thereby improves the yield of 1,2-propanediol.

Steps a) to e) of the method of the present invention are preferably carried out continuously. Steps d) and e) for extracting and recycling tungsten allow for continuous operation of the method with a reduced consumption of tungsten, i.e. a reduced need of feeding a tungsten compound to step a) for maintaining catalyst activity of the catalyst mixture.

In a preferred embodiment of the method of the present invention, recycling step c) comprises a step of subjecting at least a part of the separated organic phase ($P_o$) to a nanofiltration providing a retentate enriched in heteropolytungstate and a permeate depleted in heteropolytungstate. The retentate provided by the nanofiltration is recycled to the reaction step a) and the permeate provided by the nanofiltration is passed to step d) to provide at least part of said extractant solution. The term nanofiltration here refers to a pressure-driven separation of a solution where a part of the solvent permeates through the membrane to give a permeate and the membrane retains particles and dissolved molecules which having a diameter of less than 2 nm in the part of the solution which has not permeated the membrane and forms the retentate, corresponding to the nomenclature recommendation of IUPAC. A nanofiltration membrane is used for this nanofiltration which retains the salt of peroxotungstate or heteroperoxotungstate and the cation of the phase transfer catalyst in the retentate and allows the solvent (S) to pass through the membrane and into the permeate. The nanofiltration is preferably operated such that the concentration of the salt of peroxotungstate or heteropolyperoxotungstate and the cation of the phase transfer catalyst in the retentate does not increase above the saturation concentration. Preferably, the part of the organic phase ($P_o$) which is subjected to nanofiltration is combined with the extract phase ($P_e$) prior to passing it to the nanofiltration. This can be used to reduce the concentration of peroxotungstate or heteropolyperoxotungstate in the feed of the nanofiltration which allows to provide more permeate without exceeding the saturation limit on the retentate side.

Membranes based on the polymers polyimide, polyether sulfone, polyamide and polidimethylsiloxane can be used for the nanofiltration. Suitable nanofiltration membranes are commercially available, for example, from Evonik Membrane Extraction Technology MET under the name PuraMem@ S600, from GMT Membrantechnik under the name ONF-2, from SolSep under the designations 010306, 030306, 030705 and 030306F, and from AMS Technologies under the name NanoPro™ SX. Preferably, a composite membrane known from DE 195 07 584, EP 1 741 481 and WO 2011/067054 is used for the nanofiltration.

The nanofiltration is preferably carried out as a cross-flow filtration, preferably at a temperature in the range of from 20 to 90° C., particularly preferably from 40 to 80° C. The transmembrane pressure is preferably 2 to 5 MPa. The pressure on the retentate side can be up to MPa. The pressure on the permeate side is preferably adjusted to be high enough to prevent desorption of propene or oxygen, which enter the nanofiltration dissolved in organic phase ($P_o$), on the permeate side of the nanofiltration membrane. When step c) comprises a nanofiltration step, it may also comprise a step of desorbing propene and oxygen from the part of the organic phase ($P_o$) subjected to nanofiltration prior to the nanofiltration step. Such desorption prior to nanofiltration allows operating the nanofiltration with a lower permeate side pressure. In the alternative, propene and oxygen may also be desorbed from the permeate prior to passing the permeate to the extraction step to prevent desorption of gaseous propene and oxygen in the extraction step. In a further alternative, step d) of extracting may be carried out at a pressure which prevents desorption of propene and oxygen dissolved in the permeate which is passed to the extraction step. Preferably, phase transfer catalyst is added to the nanofiltration permeate before passing it to extraction step d), preferably in an amount providing the molar ratio of phase transfer catalyst contained in the extractant solution to tungsten contained in the aqueous phase ($P_a$) specified further above. Preferably, the nanofiltration permeate with added phase transfer catalyst is used as the extractant solution in extraction step d).

The method of the invention can be carried out in the facility of the invention.

The facility of the invention comprises a cooled loop reactor (1) which comprises an inlet (2) for hydrogen peroxide, an inlet (3) for propene, an outlet (4) for reaction mixture, and at least one recycle stream inlet (5). The loop reactor may comprise any kind of heat exchanger (27) for effecting the cooling and preferably comprises a plate heat exchanger or a tube bundle heat exchanger which is preferably configured for reaction mixture passing through the tubes. The loop reactor typically further comprise a circulation pump (26) and a circulation conduit (28), as well as inlets for hydrogen peroxide, the propene feedstock and heteropolytungstate. When a polytungstophosphate is used as heteropolytungstate, the loop reactor may comprise inlets for phosphoric acid (21) and for a tungstate (29), such as sodium tungstate. The outlet (4) for reaction mixture is preferably located at the uppermost point of the loop, which allows for operating the loop reactor (1) flooded with the liquid reaction mixture, i.e. without a continuous gas phase inside the loop reactor (1).

The facility of the invention further comprises a phase separator (6) which comprises an inlet, a first outlet for separated aqueous phase and a second outlet for separated organic phase. The inlet of the phase separator (6) is connected by a conduit (7) to the outlet (4) of the loop reactor (1) for receiving reaction mixture. The outlet for separated organic phase is preferably located at the uppermost point of the phase separator (6), which allows for operating the phase separator (6) flooded with the liquid reaction mixture, i.e. without a continuous gas phase inside the phase separator (6). The phase separator (6) preferably comprises a settler vessel. A coalescer element (not shown in the figure) comprising a structured packing or a random packing with a surface wetted by the dispersed phase of the two-phase mixture may be arranged in the phase separator (6) or upstream of the phase separator (6). The phase separator (6) may also comprise an inlet for an aqueous sulfate solution (not shown in the figure) which is preferably located on the upstream conduit (7) and, if a coalescer is present, is preferably located upstream of the coalescer.

The facility of the invention also comprises a membrane nanofiltration unit (8) having an inlet, a first outlet for retentate and a second outlet for permeate. The inlet is connected to the second outlet of the phase separator (6) by a conduit (9) for receiving all or a part of the separated organic phase. The first outlet is connected to a recycle stream inlet of the loop reactor by a conduit (10). The membrane nanofiltration unit is preferably configured for cross flow filtration on the retentate side of the membrane. The membrane nanofiltration unit may comprise several nanofiltration modules arranged in parallel, preferably spiral wound nanofiltration modules.

The facility of the invention comprises an extraction unit (11), having a feed inlet, an extractant inlet, an extract outlet and a raffinate outlet. The feed inlet is connected to the first outlet of the phase separator (6) by a conduit (12) for receiving the separated aqueous phase. The extractant inlet is connected to the second outlet of the membrane nanofiltration unit (8) by a conduit (13) for receiving the permeate. The extraction unit (11) may comprise a combination of a mixer and a downstream settler with the feed inlet and the extractant inlet on the mixer and the extract outlet and the raffinate outlet on the settler. In a preferred alternative, the extraction unit (11) comprises a counter current extraction column. For use with a solvent (S) having a density lower than the density of water, the extraction column preferably has the feed inlet near the top of the extraction column, the extractant inlet below the feed inlet and near the bottom of the extraction column, the extract outlet at the top of the extraction column, and the raffinate outlet at the bottom of the extraction column. Preferably, there is also an inlet for phase transfer catalyst on the conduit (13) which connects the second outlet of the membrane nanofiltration unit (8) with the extractant inlet of the extraction unit (11).

The facility of the invention also comprises a first recycle conduit (14) which connects the extract outlet of the extraction unit (11) with the inlet of the membrane nanofiltration unit (8) or with a recycle stream inlet of the loop reactor (1) or with both of these inlets. The first recycle conduit (14) is preferably connected with the inlet of the membrane nanofiltration unit (8). The facility preferably comprises a second recycle conduit (15) which connects the second outlet of the phase separator (6) to an inlet of the loop reactor (1) for receiving the fraction of the separated organic phase which is not passed to the membrane nanofiltration unit (8) as a recycle stream. The facility will typically also comprise a controller and a control valves not shown in the figure for adjusting and controlling the fraction of the separated organic phase which is passed to the membrane nanofiltration unit (8).

The facility of the invention further comprises a separation unit (16) which has an inlet connected to the raffinate outlet of the extraction unit (11), an outlet for separated water, an outlet for separated 1,2-propanediol and an outlet for by-products. The separation unit (16) preferably comprises a series of at least two distillation columns with a first distillation column (17), which has a bottoms outlet and an inlet providing the inlet of the separation unit (16), and a second distillation column (18). The second distillation column (18) has an inlet connected to the bottoms outlet of the first distillation column (17), an overhead product outlet for separated 1,2-propanediol and a bottoms outlet for by-products.

The facility of the invention preferably comprises an additional hydrogenation unit (19) arranged between the raffinate outlet of the extraction unit (11) and the inlet of the separation unit (16). The hydrogenation unit (19) preferably comprises a fixed bed reactor, preferably configured for trickle bed operation, for hydrogenating the separated aqueous phase with hydrogen in the presence of a heterogeneous hydrogenation catalyst.

In a preferred embodiment, the facility of the invention additionally comprises a catalyst reactivation unit (20) which comprises inlets (21, 22) for phosphoric acid and for hydrogen peroxide, an inlet (23) connected to the second outlet of the phase separator (6) for receiving a fraction of the separated organic phase, a mixing device (24) downstream of the inlets, and an outlet downstream of the mixing device (24). The outlet of the catalyst reactivation unit (20) is connected by a conduit (25) to an inlet of the loop reactor (1) for receiving the organic phase formed in the catalyst reactivation unit (20) as a recycle stream. The mixing device may be a stirred vessel or may be a loop reactor as described further above. The outlet of the catalyst reactivation unit (20) may be configured to receive the entire two-phase mixture formed in the catalyst reactivation unit (20) or may comprise a settler for receiving only the organic phase of the mixture formed in the catalyst reactivation unit (20). When such a settler is present, it will typically also have an outlet for aqueous phase connected to an inlet of the catalyst reactivation unit (20) for recycling a part of the aqueous phase to the catalyst reactivation and to an inlet of the cooled loop reactor (1) for passing a part of the aqueous phase to the propene oxidation reaction.

The present invention will now be explained in more detail with reference to an example.

EXAMPLES

Example

Preparation of Initial Epoxidation Catalyst Solution 324 g of an aqueous solution containing 7.2% by weight of sodium tungstate dihydrate, 23.1% by weight of phosphoric acid and 7.1% by weight of hydrogen peroxide were stirred for 12 h at room temperature. Then, a solution of 122 g of methyltri(octyl/decyl)ammonium methylsulfate (CAS No. 2387913-24-6) in 990 g Hydrosol A 200 ND (a mixture of C10 alkyl benzenes) was added and the mixture was stirred for another 2 h at room temperature. The aqueous and organic phases were then separated to provide 1148 g of organic phase as initial epoxidation catalyst solution.

Reaction of Propene with Hydrogen Peroxide

The reaction of propene with hydrogen peroxide was carried out at a temperature of 80° C. and a pressure of 3.3 MPa in a loop reactor with a loop volume of 0.5 I, a circulation pump and a heat exchanger for adjusting the reaction temperature, which was operated at a circulation rate of 70 kg h$^{-1}$. The reactor was equipped with a catalyst feed reservoir and feed pumps for feeding liquid propene, liquid propane, an aqueous hydrogen peroxide solution and liquid from the catalyst feed reservoir. The initial epoxidation catalyst solution was charged to the catalyst feed reservoir. The loop initially contained reaction mixture from a previous experiment. Circulation was started and maintained at 70 kg h$^{-1}$ and the circulating mixture was heated to 80° C. Then 80 g h$^{-1}$ of propene, 50 g h$^{-1}$ of propane, 210 g h$^{-1}$ of a 15% by weight aqueous hydrogen peroxide solution containing 0.4% by weight phosphoric acid, and 320 g h$^{-1}$ of organic catalyst solution from the catalyst feed reservoir were introduced into the loop reactor, cooling the circulating mixture to maintain a reaction temperature of 80° C. A two-phase oxidation reaction mixture was removed from the loop reactor in an amount corresponding to the amounts added. Phases were separated, the depressurized and cooled aqueous phase was allowed to stand for additional phase separation and the organic phases from the first and second phase separation were combined. The combined organic phases were passed to the catalyst feed reservoir after depressurizing and cooling to 25° C. After about 9 h of operation, the feeding of reactants and the circulation in the loop reactor were stopped. The next day, circulation in the loop reactor was restarted, dosing of reactants was resumed after the reaction temperature had been established in the loop reactor and the reaction was continued for another 11 h.

The aqueous phase from the final 10 h of operating the reaction was collected and analyzed for hydrogen peroxide by redox titration and for organic products by capillary GC (25 m CP-WAX-52 CB column from Agilent, He carrier gas, temperature program starting at 50° C. with ramps of 20 K/min to 90° C., 10 K/min to 220° C. and 5 K/min to 235° C., FID detector). The analysis showed a hydrogen peroxide conversion of 96% with the stream of aqueous phase provided by the reaction containing 630 mmol/h 1,2-propanediol, 95 mmol/h dipropylene glycol, 11 mmol/h tripropylene glycol and 12 mmol/h hydroxyacetone.

Extraction of the Separated Aqueous Phase.

800 g of the collected aqueous phase were extracted with 160 g of a solution of 1.2% by weight of methyltri(octyl/decyl)ammonium methylsulfate in Hydrosol A 200 ND by mixing for 2 h and letting the mixture stand until phases had separated. The aqueous phase was analyzed for tungsten content by ICP-OES before and after extraction, which showed a tungsten content of 63 mg/kg prior to extraction and a tungsten content of 46 mg/kg after extraction.

The extraction was repeated by extracting 800 g of the collected aqueous phase with 160 g of a solution of 8.2% by weight of methyltri(octyl/decyl)ammonium methylsulfate in Hydrosol A 200 ND. The analysis showed a tungsten content of 16 mg/kg after extraction.

LIST OF REFERENCE SIGNS

1 Cooled loop reactor
2 Inlet for hydrogen peroxide
3 Inlet for propene
4 Outlet for reaction mixture
5 Recycle stream inlet
6 Phase separator
7 Conduit connecting the loop reactor (1) with the phase separator (6)
8 Membrane nanofiltration unit
9 Conduit connecting the phase separator (6) with the membrane nanofiltration unit (8)
10 Conduit connecting the membrane nanofiltration unit (8) with the loop reactor (1)
11 Extraction unit
12 Conduit connecting the phase separator (6) with the extraction unit (11)
13 Conduit connecting the membrane nanofiltration unit (8) with the extraction unit (11)
14 Conduit connecting the extraction unit (11) with the membrane nanofiltration unit (8)
15 Conduit connecting the phase separator (6) with the loop reactor (1)
16 Separation unit 17 First distillation column
18 Second distillation column
19 Hydrogenation unit
20 Catalyst reactivation unit
21 Inlet for phosphoric acid
22 Inlet for hydrogen peroxide
23 Inlet of catalyst reactivation unit (20) connected to the phase separator (6)
24 Mixing device
25 Conduit connecting the catalyst reactivation unit (20) with the loop reactor (1)
26 Circulation pump
27 Heat exchanger
28 Circulation conduit
29 Inlet for tungstate

The invention claimed is:

1. A method for the preparation of 1,2-propanediol, comprising:
   a) reacting propene with hydrogen peroxide in the presence of a catalyst mixture, comprising a phase transfer catalyst and a heteropolytungstate, in a liquid reaction mixture comprising an aqueous phase with a maximum apparent pH of 6 and an organic phase comprising a solvent(S) having a solubility in water at 20° C. of less than 500 mg/kg, wherein apparent pH refers to a value determined by measurement with a glass electrode employing a commercial pH meter calibrated with aqueous buffer solutions of known pH for measuring dilute aqueous solutions;
   b) separating the liquid reaction mixture of a) into an aqueous phase ($P_a$) comprising 1,2-propanediol and an organic phase ($P_o$);
   c) recycling at least a part of the organic phase ($P_o$) to a);
   d extracting the aqueous phase ($P_a$) with an extractant solution comprising the same phase transfer catalyst and the same solvent(S) as used in a), to provide an extracted aqueous phase ($P_{ac}$) and an extract phase ($P_e$) comprising a salt of the phase transfer catalyst and a heteropolytungstate or tungstate;
   e) recycling at least a part of the extract phase ($P_e$) to a); and
   f) recovering the 1,2-propanediol from the extracted aqueous phase ($P_{ae}$).

2. The method of claim 1, wherein c) comprises subjecting the at least a part of the organic phase ($P_o$) to a nanofiltration providing a retentate enriched in the heteropolytungstate and a permeate depleted in the heteropolytungstate, recycling the retentate to a), and passing the permeate to d) to provide at least part of said extractant solution.

3. The method of claim 2, wherein the at least a part of the organic phase ($P_o$) subjected to nanofiltration is combined with said extract phase ($P_e$) prior to said nanofiltration.

4. The method of claim 2, wherein phase transfer catalyst is added to said permeate before passing to d).

5. The method of claim 1, wherein d) is carried out in a counter current extraction column.

6. The method of claim 1, wherein d) is carried out in an extraction unit or a series of from 2 to 5 consecutive extraction units, each extraction unit comprising a mixer and a settler in series.

7. The method of claim 1, wherein a) to e) are carried out continuously.

8. The method of claim 7, wherein a) is conducted in a loop reactor comprising fixed internals in a tubular section, and the liquid reaction mixture is passed through the loop reactor at a flow rate sufficient to provide turbulent flow at said fixed internals.

9. The method of claim 1, wherein said solvent(S) comprises at least one alkylated aromatic hydrocarbon having from 7 to 12 carbon atoms.

10. The method of claim 1, wherein the phase transfer catalyst comprises at least one selected from the group consisting of a tertiary amine, a tertiary ammonium salt, and a quaternary ammonium salt, and wherein the tertiary amine, the tertiary ammonium salt, and the quaternary ammonium salt each comprises in total at least 12 carbon atoms.

11. The method of claim 10, wherein the phase transfer catalyst comprises a tertiary or quaternary ammonium ion having the structure $R_1R^2R^3NR^{4+}$, wherein $R^1$, $R^2$, and $R^3$ are the same or different and are each an alkyl group having from 8 to 10 carbon atoms, and $R^4$ is hydrogen or methyl.

12. The method of claim 1, wherein c) comprises contacting the at least a part of the organic phase ($P_o$) with an aqueous reactivating solution comprising hydrogen peroxide and phosphoric acid, at a temperature of from 5 to 40° C.

13. The method of claim 12, wherein a further organic phase resulting from said contacting with an aqueous reactivating solution is passed to a) without any intervening steps.

14. The method of claim 12, wherein the at least a part of the organic phase ($P_o$) is combined with said extract phase ($P_e$) prior to said contacting with an aqueous reactivating solution.

\* \* \* \* \*